United States Patent
Hughes et al.

[11] Patent Number: 5,847,403
[45] Date of Patent: Dec. 8, 1998

[54] SYSTEM AND METHOD FOR REDUCING RADIATION LEAKAGE WITH INTENSITY MODULATED TREATMENTS

[75] Inventors: John H. Hughes, Martinez; Jonathan Yi Yao, Pleasant Hill; Francisco M. Hernanez-Guerra, Concord, all of Calif.

[73] Assignee: Siemens Medical Systems, Inc., Del.

[21] Appl. No.: 780,423

[22] Filed: Jan. 7, 1997

Related U.S. Application Data

[63] Continuation-in-part of Ser. No. 491,322, Jun. 30, 1995, Pat. No. 5,591,983, and a continuation-in-part of Ser. No. 665,153, Jun. 13, 1996, Pat. No. 5,668,847, which is a continuation of Ser. No. 504,937, Jul. 20, 1995, Pat. No. 5,563,925, and a continuation-in-part of Ser. No. 642,065, May 3, 1996, which is a continuation-in-part of Ser. No. 504,722, Jul. 20, 1995, Pat. No. 5,621,779.

[51] Int. Cl.[6] .................................................. G21F 5/04
[52] U.S. Cl. .................................... 250/505.1; 378/150
[58] Field of Search ..................... 250/505.1; 378/147, 378/150, 151, 152, 65

[56] References Cited

U.S. PATENT DOCUMENTS

| | | | |
|---|---|---|---|
| 4,200,799 | 4/1980 | Saito | 378/150 |
| 4,868,844 | 9/1989 | Nunan | 378/152 |
| 4,937,849 | 6/1990 | Huber et al. | 378/150 |
| 4,947,416 | 8/1990 | McFaul et al. | 378/150 |
| 5,138,647 | 8/1992 | Nguyen et al. | 378/189 |
| 5,216,255 | 6/1993 | Weidlich | 250/492.3 |
| 5,311,616 | 5/1994 | Swerdloff et al. | 378/65 |
| 5,332,908 | 7/1994 | Weidlich | 250/442.1 |
| 5,351,280 | 9/1994 | Swerdloff et al. | 378/65 |
| 5,563,925 | 10/1996 | Hernandez | 378/65 |
| 5,591,983 | 1/1997 | Yao et al. | 250/505.1 |
| 5,621,774 | 4/1997 | Hughes et al. | 378/65 |

*Primary Examiner*—Kiet T. Nguyen
*Attorney, Agent, or Firm*—Heather S. Vance

[57] ABSTRACT

A system and a method are provided for intensity modulated radiation treatment. A field on a patient (544) for irradiation is first defined. A beam of radiation (530) is then provided. This beam (530) passing through an opening defined by a beam-shielding device (540, 542). In the preferred embodiment, the beam shielding device is a single jaw (540) and a single collimator section (542). Single jaw (540) and single collimator section (542) are moved in one direction at different velocities to vary the opening for radiation beam (530). Single jaw (540) and single collimator section (542) move without rotation to provide intensity modulated radiation treatment

21 Claims, 6 Drawing Sheets

SYSTEM AND METHOD FOR REDUCING RADIATION LEAKAGE WITH INTENSITY MODULATED TREATMENTS

CROSS REFERENCE TO RELATED APPLICATION

This application is (1) a continuation-in-part of U.S. patent application Ser. No. 08/491,322, filed Jun. 30, 1995 now U.S. Pat. No. 5,591,983, (2) a continuation-in-part of U.S. patent application Ser. No. 08/665,153 filed Jun. 13, 1996 now U.S. Pat. No. 5,668,847 which is a continuation of U.S. patent application Ser. No. 08/504,937, filed Jul. 20, 1995 now U.S. Pat. No. 5,563,925, and (3) a continuation-in-part of U.S. patent application Ser. No. 08/642,065, filed May 3, 1996 (pending), which is a continuation-in-part of U.S. patent application Ser. No. 08/504,722, filed Jul. 20, 1995 now U.S. Pat. No. 5,621,779, all of which are incorporated herein by reference in their entireties for all purposes.

BACKGROUND OF THE INVENTION

1. Field of the Invention

The invention relates to a radiation emitting device, and more particularly to a system and a method for reducing the radiation leakage associated with intensity modulated treatments.

2. Description of the Related Art

Radiation-emitting devices are generally known and used, for instance, as radiation therapy devices for the treatment of patients. A radiation therapy device usually comprises a gantry, which can be swiveled around a horizontal axis of rotation in the course of a therapeutic treatment. A linear accelerator is located in the gantry for generating a high-energy radiation beam for therapy. This high energy radiation beam can be an electron radiation or photon (X-ray) beam. During treatment, this radiation beam is trained on a zone of a patient lying in the isocenter of the gantry rotation. Radiation treatment devices have built in safety schemes that give the user confidence that the correct radiation is being delivered. However, it is hard to guarantee the delivery of radiation to the treatment site.

Before treatment, a patient may be scanned with a computer tomograph (CT), and/or treatment may be simulated with a diagnostic X-ray unit (i.e., a simulator). These devices identify the area in the body to be irradiated and the surrounding critical organs. The physician determines a method of treatment based on the patient's weight and age, along with the type and size of the diseased area. Data from the CT and/or the simulator along with the radiation emitting device data are used in the treatment planning process to calculate the dose levels which are to be delivered to the treatment site. The treatment plan also calculates the radiation exposure to healthy tissue. The physician approves the plan, which is then transferred to the radiation emitting device.

To control the radiation emitted toward a patient, a beam-shielding device such as a plate arrangement and/or collimator is usually provided in the trajectory of the radiation beam between the radiation source and the patient. An example of a plate arrangement is a set of four plates which can be used to define an opening for the radiation beam. The beam-shielding device defines a field on the patient to which a prescribed amount of radiation is to be delivered. A collimator is a beam-shielding device which usually includes multiple leaves (e.g., 50 leaves). These leaves are positioned to accurately direct the radiation beam toward the area to be treated with radiation. While these leaves provide an accurate definition of the area to be treated with radiation, they also allow for a small amount of undesirable radiation leakage. This leakage occurs between the leaves.

U.S. patent application Ser. No. 08/642,065, filed May 3, 1996, describes a system and a method for verifying the amount of radiation delivered to a patient. U.S. patent application Ser. No. 08/504,722, filed Jul. 20, 1995, describes a system and a method for delivering and displaying radiation delivered to a predetermined field on a patient. U.S. Pat. No. 5,138,647 describes a portal imaging device in which an image converter plate is arranged beneath the patient. The plate converts an image represented by the radiation beam into a visible image. A reflector directs the visible image to a video camera. Such an imaging device allows the user the ability to view the anatomy of the patient during radiation treatment, but it does not give the user any idea of the quantity of radiation being delivered either to the diseased area or to the critical surrounding organs and tissue. The portal imaging device assists the user in verifying that the patient is correctly positioned during the radiation treatment. Should the patient move or be incorrectly positioned, the treatment can be stopped and the patient repositioned manually.

Intensity modulated treatment is a specialized technique for radiation treatment. Usually, the beam-shielding device in intensity modulated treatment includes either (1) two pairs of opposing jaws or (2) a pair of jaws and a pair of opposing sets of multi-leaf collimator leaves. One pair of these jaws or the pair of multi-leaf collimator leaves move in the same direction at different speeds. This creates a sweeping opening for the radiation beam. Because the jaws (or leaves) are traveling at different speeds, the opening varies in size during the sweeping. Usually, elaborate speed control and thick jaws (or leaves) are needed for intensity modulated treatment. The speed control is needed for accurately defining the changing opening size. The thick jaws (or leaves) are needed because of a concern with radiation leakage. For example, due to the sweeping treatment, approximately three times the regular amount of radiation dose is needed to treat an area on a patient. Therefore, the radiation leakage for intensity modulated treatment is approximately three times greater than regular leakage. For example, a regular treatment of 100 monitor units (MU) of radiation results in approximately 0.5 MU of radiation leakage. With an intensity modulated treatment for the same field, 300 MU of radiation is required and results in 1.5 MU of radiation leakage.

Intensity modulated treatment usually utilizes a multi-leaf collimator. The multi-leaf collimator can be in addition to the jaws, replace a pair of jaws, or replace all of the jaws. This collimator is typically rotated around the patient during the radiation treatment to provide more accurate radiation coverage. The leaves in the collimator each have a motor and two sensors. The sensors monitor the position of each of the leaves. Unfortunately, standard multi-leaf collimators usually have radiation leakage of approximately 0.5% to 1.5%. When multi-leaf collimators are used with intensity modulated treatment, the deposited radiation leakage increases due to the required increase in radiation dose. This is an unacceptable amount of radiation leakage to healthy tissue.

To reduce radiation leakage, a tongue and groove interlocking between the leaves can be used. In addition, the leaves can be placed in two interspaced layers. This technique is described more fully in U.S. patent application Ser. No. 08/491,322, filed Jun. 30, 1995.

The delivery of radiation by a radiation therapy device is prescribed and approved by an oncologist. Actual operation of the radiation equipment, however, is normally done by a therapist. When the therapist administers the delivery of the radiation treatment as prescribed by the oncologist, the radiation-emitting device is programmed to deliver that specific treatment. When programming the treatment, the therapist has to take into consideration the actual radiation output and has to adjust the dose delivery based on the plate arrangement opening to achieve the prescribed radiation treatment at the target depth in the patient. This adjustment can be made according to known calculations, but the therapist normally has to do them manually, which can lead to errors. In the context of radiation therapy, a miscalculation can lead to either a dose that is too low and is ineffective, or that is too high and dangerous. For example, a large error (e.g., a misplaced decimal point) can be lethal.

What is needed is a method, and a corresponding system, for reducing radiation leakage in an intensity modulated radiation treatment. Also, a system which provides efficient and accurate delivery of intensity modulated radiation treatment is desired.

SUMMARY OF THE INVENTION

According to the invention, a system and a method are provided for intensity modulated radiation treatment. A field on a patient for irradiation is first defined. A beam of radiation is then provided. This beam passing through an opening defined by a beam-shielding device. In the preferred embodiment, the beam shielding device is a single jaw and a single collimator section. The single jaw and the single collimator section are moved in one direction at different velocities to vary the opening for the radiation beam. The single jaw and the single collimator section move without rotation to provide intensity modulated radiation treatment.

DETAILED DESCRIPTION

The invention is described below with primary reference to a system for delivering X-ray radiation to a field on a patient, and for delimiting the field using at least one movable plate or jaw in the beam path from a radiation source. The invention may be used to control the delivery of any type of energy, for example, electrons (instead of X-rays), to any type of patient (not just a human patient), provided the amount of energy delivered to the field can be sensed or estimated.

Figure 1A:
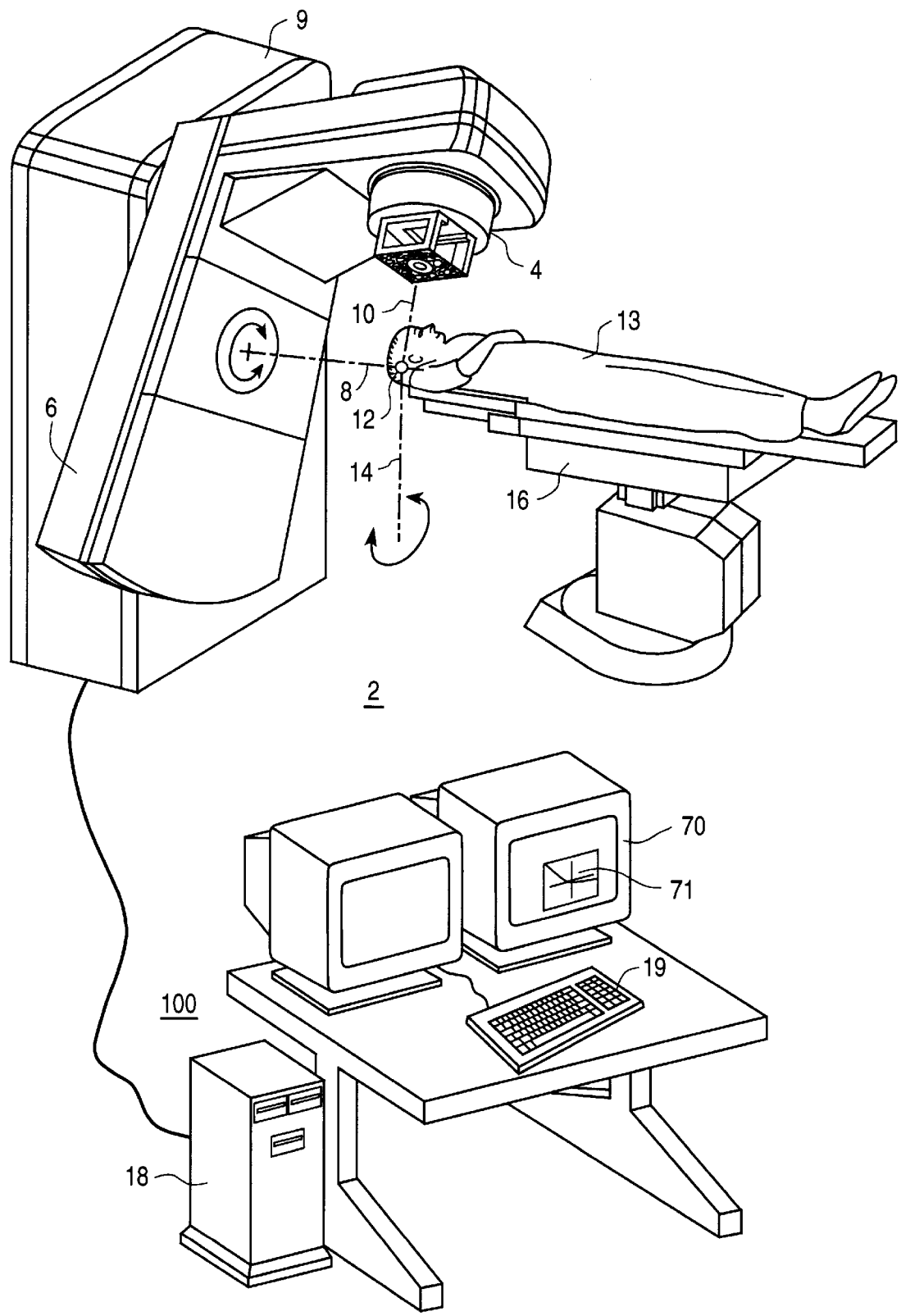
FIG. 1A shows a schematic diagram of a radiation treatment device including a treatment console constructed in accordance with the present invention.
Figure 1B:
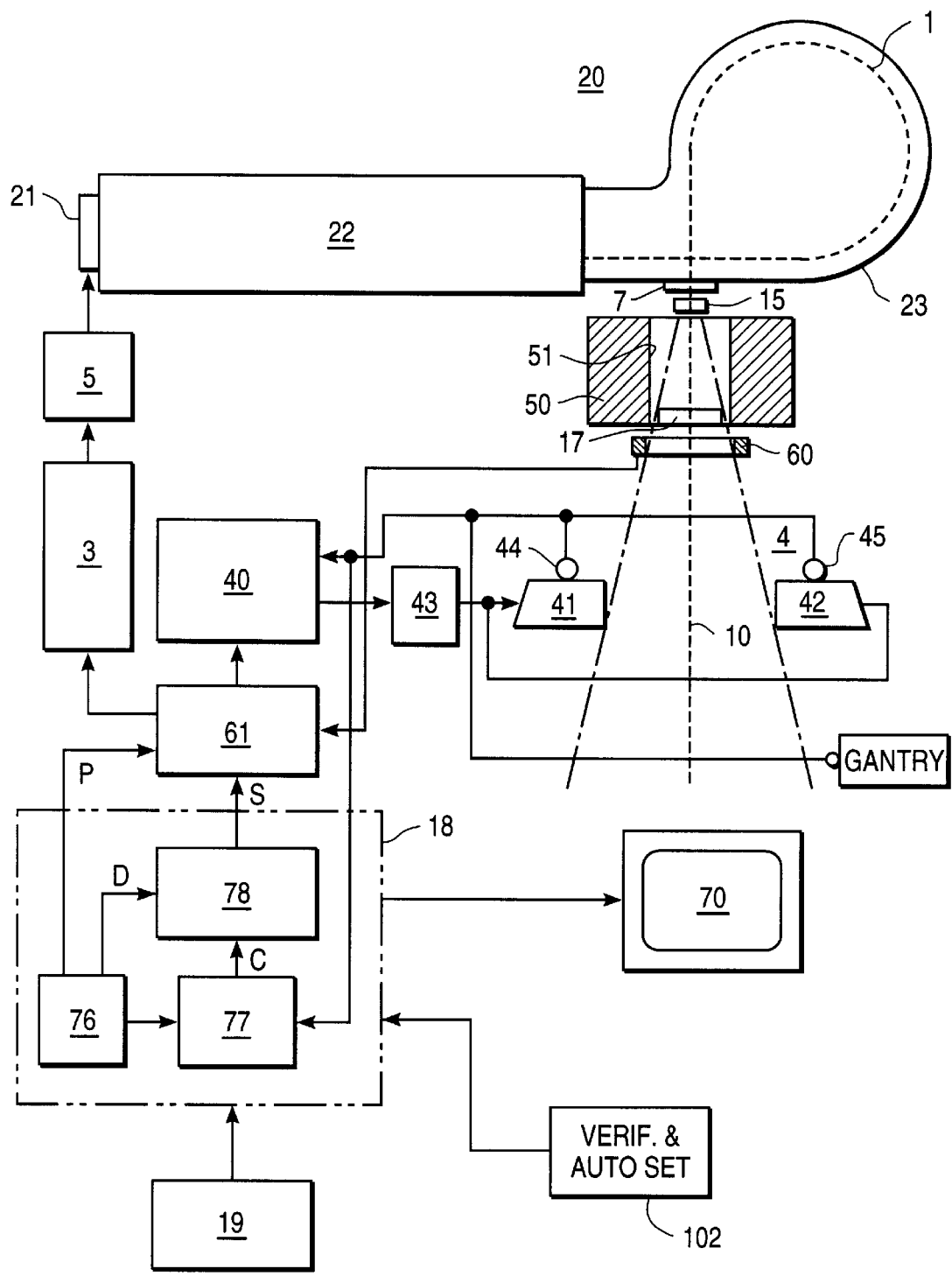
FIG. 1B shows portions of an illustrative radiation treatment device 2 and portions of treatment unit 100 in more detail

FIG. 1 shows a radiation treatment device 2 of common design, in which plates 4, a control unit in a housing 9 and a treatment unit 100 are used. The radiation treatment device 2 comprises a gantry 6 which can be swiveled around a horizontal axis of rotation 8 in the course of a therapeutic treatment. Plates 4 are fastened to a projection (e.g., an accessory holder) of gantry 6. To generate the high-powered radiation required for the therapy, a linear accelerator is located in gantry 6. The axis of the radiation beam emitted from the linear accelerator and gantry 6 is designated by 10. Electron, photon, or any other detectable radiation can be used for the therapy. During the treatment, the radiation beam is trained on a zone 12 of a patient 13. Rotational axis 8 of gantry 6, rotational axis 14 of the area on the patient to be treated, and beam axis 10 all preferably intersect in the isocenter.

The area of the patient that is irradiated is known as the field. Plates 4 are substantially impervious to the emitted radiation. They are mounted between the radiation source and the patient to delimit the radiation beam to, approximately, the shape of the field. Areas of the body (e.g., healthy tissue) are therefore subjected to as little radiation as possible, and preferably to none at all.

Radiation treatment device 2 also includes a central treatment processing or control unit 100, which is usually located apart from radiation treatment device 2. The radiation treatment device 2 is normally located in a different room to protect the therapist from radiation. Treatment unit 100 includes output devices, such as at least one visual display unit or monitor 70, and an input device, such as a keyboard 19. Data can also be input through data carriers, such as data storage devices, or a verification and recording or automatic set-up system. The treatment processing unit 100 is typically operated by the therapist who administers actual delivery of a radiation treatment as prescribed by an oncologist. By utilizing the keyboard 19, or other input device, the therapist enters into a control unit 18 of treatment unit 100 the data that defines the radiation to be delivered to the patient (e.g., according to the prescription of the oncologist). The program can also be input via another input device like a data storage device, through data transmission or using the automatic set-up system. Various data can be displayed before, during and after the treatment on screen 71 of monitor 70.

Plate arrangement 4 can include a pair of aperture jaws located opposite each other and an additional pair of aperture jaws arranged perpendicular to the first pair of jaws. To match the size of the field to be irradiated, each of the aperture jaws can be moved with respect to axis 10 by a drive unit. The drive unit comprises an electric motor which is coupled to the jaws and controlled by a motor controller. Position sensors can be coupled to the jaws for sensing their positions. In another arrangement, the plates are replaced with a multi-leaf collimator containing many (e.g., 60) radiation blocking leaves.

Figure 2:
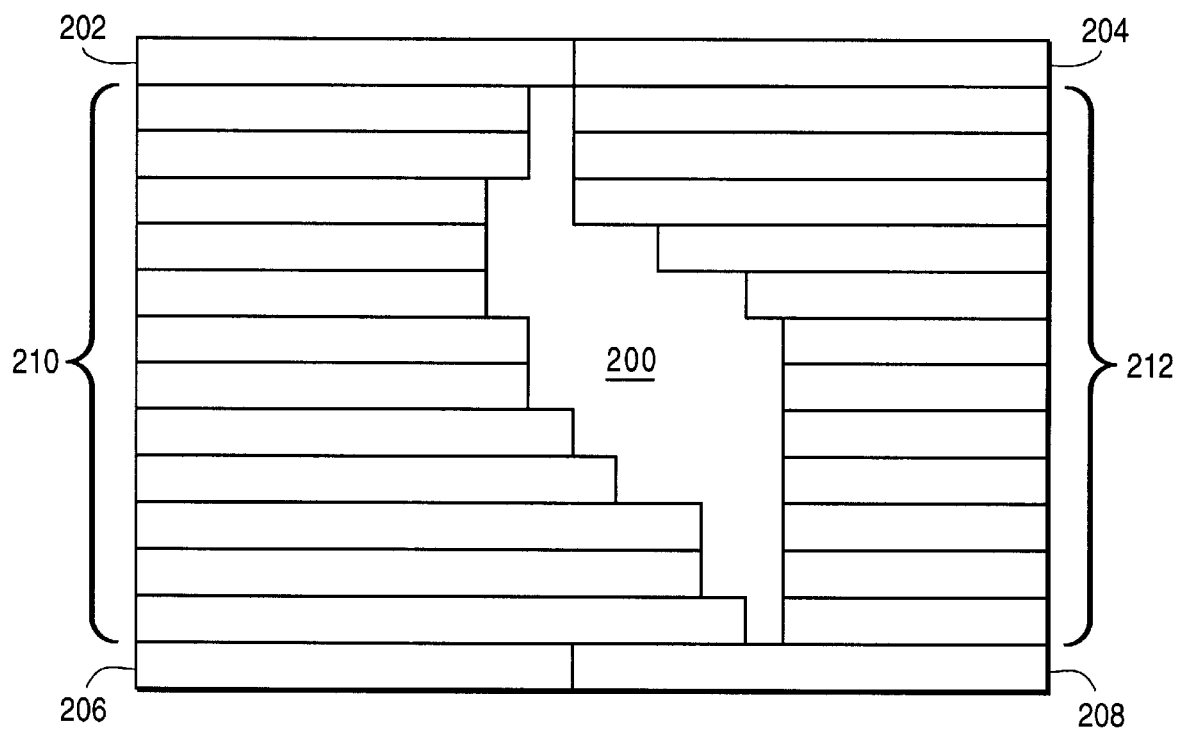
FIG. 2 illustrates how a multi-leaf collimator can act as a beam-shielding device.

As stated above, when a multi-leaf collimator is used, radiation leakage occurs between the multiple leaves. To reduce this leakage, the thickness of the leaves can be increased. Presently, a multi-leaf collimator is used in addition to two sets or one set of jaws. If all of the jaws are removed, a multi-leaf collimator alone can be used as the beam-shielding device. FIG. 2 illustrates how a multi-leaf collimator can act as a beam-shielding device. In the preferred embodiment, opening 200 is created by two sets of leaves 202, 204, 206, 208, 210, 212 in a multi-leaf collimator. First set of leaves 202, 206, 210 extend toward opening 200 from the left, and second set of leaves 204, 208, 212 extend toward opening 200 from the right. Additional jaws are not needed because the outermost leaves 202, 204, 206, 208 are completely closed to provide upper and lower boundaries for opening 200.

If all of the jaws are removed from the radiation treatment device, there is more space vertically for thicker multi-leaf collimator leaves. As shown in FIG. 1, removing plates/jaws 4 would provide more space between gantry 6 and patient 13. Therefore, thicker leaves can be used to reduce radiation leakage. For example, if the standard leaf thickness normally provides 1% radiation leakage, doubling the thickness of the leaves results in approximately 0.5% radiation leakage. In the preferred embodiment, the leaves consist of a metal which blocks radiation (e.g., tungsten).

In another embodiment of the present invention, more leaves are used in the multi-leaf collimator. Each leaf has a shorter width. For example, thirty 1.0 cm wide leaves can be replaced by sixty 0.5 cm wide leaves. This results in an opening which matches the area to be treated with radiation better. With the improved resolution, collimator rotation is not needed for the intensity modulated treatment. When more leaves are used, there are more gaps between the leaves. Thus, changes must be made to reduce the radiation leakage occurring between these additional gaps. For example, as stated above, the thickness of the leaves can be increased.

Figure 3:
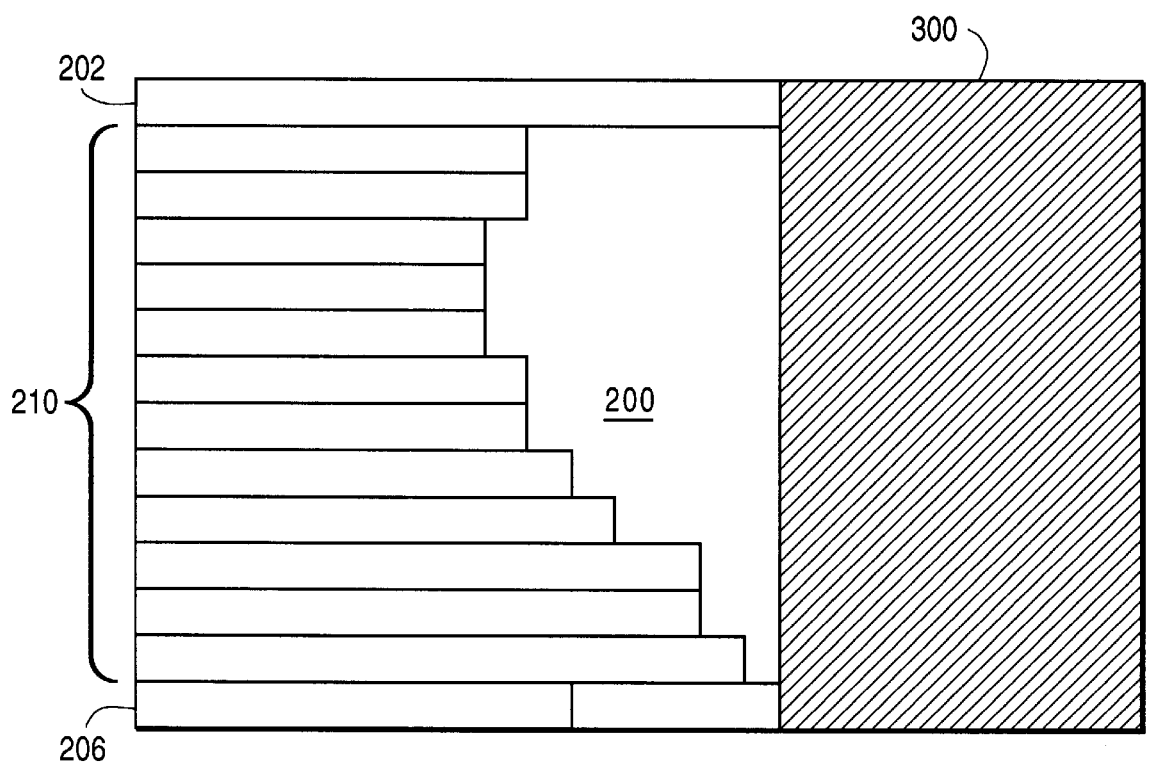
FIG. 3 illustrates a configuration which uses one set of multi-leaf collimator leaves and one jaw.

In another embodiment of the present invention, one side of the multi-leaf collimator is removed and replaced with a single jaw. FIG. 3 illustrates a configuration which uses one set of multi-leaf collimator leaves and one jaw. In this arrangement, the second set of multi-leaf collimator leaves is replaced by jaw 300. Opening 200 is then defined by jaw 300 and first set of multi-leaf collimator leaves 202, 206, 210. Because of the sweeping approach utilized in the present invention, first set of multi-leaf collimator leaves 202, 206, 210 and jaw 300 provide enough resolution for accurate radiation treatment. This configuration is less expensive because it is much easier to manufacture a rectangular jaw rather than a set of multiple leaves for a collimator. For example, half of the motors and position sensors which are used with the leaves are no longer needed in this arrangement. Additionally, half of the leakage from gaps between the leaves is eliminated when half of the leaves are replaced by jaw 300.

Figure 4:
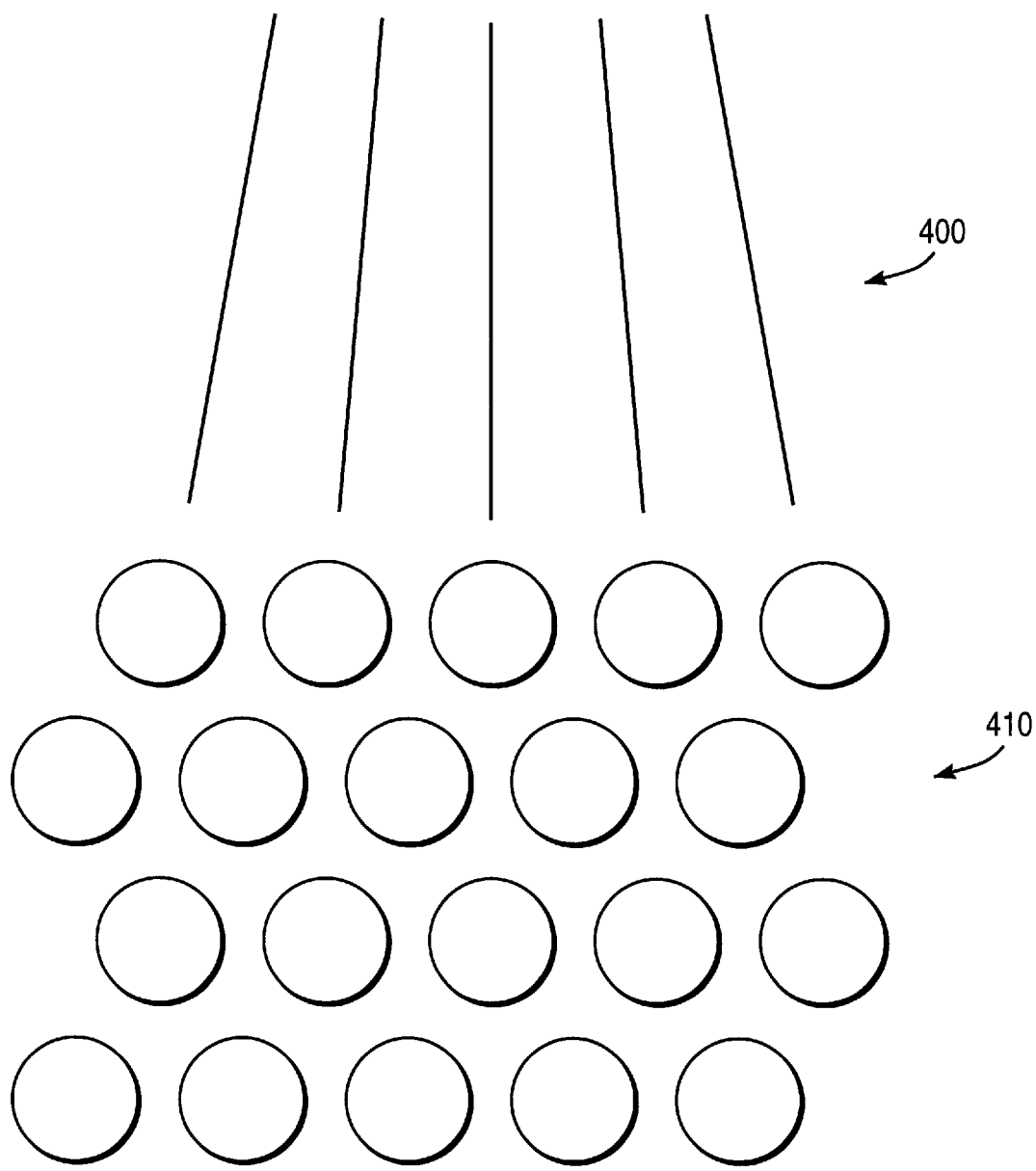
FIG. 4 provides a configuration of rods for the present invention.

In yet another embodiment of the present invention, the leaves of the multi-leaf collimator are replaced with multiple layers of rods. FIG. 4 provides a configuration of rods for the present invention. In the preferred embodiment, radiation beam 400 can be effectively blocked by rods 410. By providing rows of rods 410 which overlap, leakage between the rods is minimized. The number of rows of rods 410 is variable. Thus, the number of rows of rods 410 can be changed to meet a particular radiation leakage requirement. By providing rods 410 with small diameters, the shape of the field to be treated with radiation can be easily matched. Again, these rods 410 consist of a material which blocks radiation (e.g., tungsten).

Figure 5:
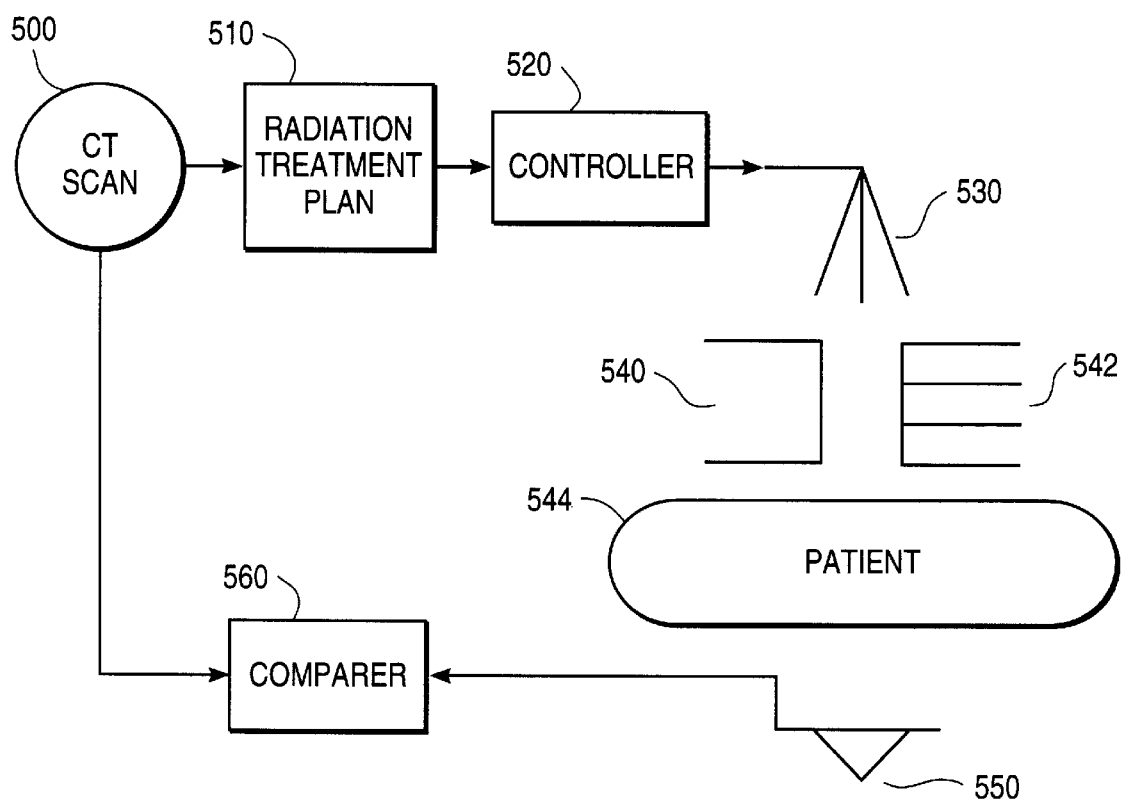
FIG. 5 shows an overall configuration for radiation treatment which uses the present invention.

FIG. 5 shows an overall configuration for radiation treatment which uses the present invention. A computer tomograph (CT) scan 500 is provided to create radiation treatment plan 510. Elaborate software can be used to automatically create treatment plan 510, or a user can create treatment plan 510. Both the software and the user utilize information from CT scan 500 when creating treatment plan 510. Controller 520 determines the amount and duration of radiation 530 for radiation treatment plan 510. Radiation 530 is then partially blocked by jaw 540 and leaves 542 before reaching the patient. Exit dose verification 550 monitors the amount of radiation 530 exiting the patient 544. Comparer 560 compares the readings from exit dose verification 550 with CT scan 500. If a discrepancy is found, information is sent from comparer 560 to controller 520 such that the amount of radiation 530 can be altered to correct the discrepancy. This can be referred to as exit dose verification. In the preferred embodiment, this is done during the radiation treatment to insure the correct amount of radiation is being delivered to the patient.

In yet another embodiment of the present invention, a virtual wedge can be used with the sweeping of intensity modulated treatment. As set forth in U.S. patent application Ser. No. 08/504,937, filed Jul. 20, 1995, a physical wedge is replaced with a software program which uses the radiation blocking elements to simulate the physical wedge. Thus, jaw 540 and leaves 542 are moved in a pattern which simulates a physical wedge.

We claim:

1. A method for intensity modulated radiation treatment, comprising the steps of:

defining an irregular field on a patient for irradiation;

providing a beam of radiation, the beam passing through an opening defined by a single jaw and a single collimator section, and the beam treating the irregular field with radiation; and moving the single jaw and the single collimator section in one direction, the single jaw and the single collimator section moving at difference speeds to vary the opening for the radiation beam;

wherein the single jaw and the single collimator section move without rotation to provide intensity modulated radiation treatment to the irregular field;

whereby radiation leakage is reduced.

2. The method for intensity modulated radiation treatment of claim 1, wherein the collimator includes leaves in multiple rows.

3. The method for intensity modulated radiation treatment of claim 1, wherein the collimator includes rods in multiple rows.

4. The method for intensity modulated radiation treatment of claim 1, further comprising the step of verifying the amount of radiation delivered to the patient during radiation treatment.

5. The method for intensity modulated radiation treatment of claim 1, wherein the single jaw and the single collimator section move to simulate a physical wedge.

6. A method for intensity modulated radiation treatment, comprising the steps of:

defining an irregular field on a patient for irradiation;

providing a beam of radiation, the beam passing through an opening defined by a single collimator without jaws, the single collimator including two sections; and moving the single collimator in one direction, the sections of the single collimator moving at different speeds to vary the opening for the beam;

wherein the single collimator moves without rotation to provide intensity modulated radiation treatment.

7. The method for intensity modulated radiation treatment of claim 6, wherein the single collimator includes leaves such that, during radiation treatment, the leaves move without rotation.

8. The method for intensity modulated radiation treatment of claim 6, wherein the single collimator includes multiple rows of rods.

9. The method for intensity modulated radiation treatment of claim 6, further comprising the step of verifying the amount of radiation delivered to the patient during radiation treatment.

10. The method for intensity modulated radiation treatment of claim 6, wherein the single collimator moves to simulate a physical wedge.

11. A method for intensity modulated radiation treatment, the method comprising the steps of:

inputting parameters of an irregular field on a patient for irradiation;

creating a radiation treatment plan;

treating the irregular field with a radiation beam;

delimiting the radiation beam with beam-shielding means, the beam-shielding means moving in the same direction;

checking radiation which passes through the patient for discrepancies; and correcting any discrepancies.

12. The method for intensity modulated radiation treatment of claim 11, wherein the correcting is done by changing the radiation beam.

13. The method for intensity modulated radiation treatment of claim 11, wherein the correcting occurs during a radiation treatment.

14. The method for intensity modulated radiation treatment of claim 11, wherein the beam-shielding means consists of a single jaw and a single collimator section.

15. A system for intensity modulated radiation treatment, comprising:

means for defining an irregular field for radiation treatment;

a radiation source for generating and outputting a radiation beam; and beam-shielding means for delimiting the radiation beam to the irregular field on a patient to be treated with radiation, the beam-shielding means moving in one direction to provide a sweeping motion;

wherein the beam-shielding means provides for intensity modulated radiation without rotation of the beam-shielding means during radiation treatment.

16. The system for intensity modulated radiation treatment of claim 15, further comprising a verification system for verifying and correcting an amount of radiation delivered to the patient.

17. The system for intensity modulated radiation treatment of claim 16, wherein the verifying and the correcting are done during radiation treatment.

18. The system for intensity modulated radiation treatment of claim 15, wherein the beam-shielding means are moved to simulate a physical wedge.

19. The system for intensity modulated radiation treatment of claim 15, wherein the beam-shielding means consist of a single collimator without jaws.

20. The system for intensity modulated radiation treatment of claim 15, wherein the beam-shielding means consist of a single jaw and a single collimator section.

21. The system for intensity modulated radiation treatment of claim 15, wherein the beam-shielding means includes multiple rows of rods.

* * * * *

UNITED STATES PATENT AND TRADEMARK OFFICE
CERTIFICATE OF CORRECTION

PATENT NO. : 5,847,403
DATED : December 8, 1998
INVENTOR(S) : John H. Hughes, et. al.

It is certified that error appears in the above-indentified patent and that said Letters Patent is hereby corrected as shown below:

Title page, item [75], inventor: should read --Hernandez--.

Signed and Sealed this

Nineteenth Day of October, 1999

Attest:

Q. TODD DICKINSON

*Attesting Officer*  *Acting Commissioner of Patents and Trademarks*